United States Patent [19]

Zuk et al.

[11] Patent Number: 4,654,300

[45] Date of Patent: Mar. 31, 1987

[54] FLUORESCENT MICROBEAD QUENCHING ASSAY

[75] Inventors: Robert F. Zuk, Menlo Park; David J. Litman, Mountain View, both of Calif.

[73] Assignee: Syntex (U.S.A.) Inc., Palo Alto, Calif.

[21] Appl. No.: 364,831

[22] Filed: Apr. 2, 1982

[51] Int. Cl.[4] .................. G01N 33/54; G01N 33/546; C12N 9/96

[52] U.S. Cl. ....................................... 435/7; 436/533; 436/534; 435/810; 435/188

[58] Field of Search ................. 435/7, 14, 25, 28, 188, 435/810; 436/527, 533, 534, 546

[56] References Cited

U.S. PATENT DOCUMENTS

| | | | |
|---|---|---|---|
| 4,115,535 | 9/1978 | Giaever | 436/527 |
| 4,211,845 | 7/1980 | Genshaw et al. | 435/14 |
| 4,261,968 | 4/1981 | Ullman et al. | 435/7 |
| 4,275,149 | 6/1981 | Litman et al. | 435/7 |
| 4,299,916 | 11/1981 | Litman et al. | 435/7 |
| 4,318,707 | 3/1982 | Litman et al. | 435/7 |
| 4,366,241 | 12/1982 | Tom et al. | 435/7 |

OTHER PUBLICATIONS

Elias, "A Rapid, Sensitive Myeloperoxidase Stain Using 4-Chloro-1-Naphthol", American Journal of Clinical Pathology 73(6) (1980), pp. 797-799.

Primary Examiner—Charles F. Warren
Assistant Examiner—John E. Tarcza
Attorney, Agent, or Firm—Theodore J. Leitereg; Bertram I. Rowland

[57] ABSTRACT

Method and compositions for performing immunoassays having conjugated fluorescent particles and conjugated catalyst where the particles and catalysts are conjugated to members of a specific binding pair. Bound to the fluorescent particle is a catalyst, usually enzyme, member of a signal producing system, which system includes the fluorescent particle. Another catalyst is bound to a specific binding pair member. The catalyst-specific binding member conjugate becomes bound to the particle, by the intermediacy of the binding of the specific binding pair, producing a quenching product which binds to the particle, resulting in a reduction in fluorescence.

16 Claims, No Drawings

FLUORESCENT MICROBEAD QUENCHING ASSAY

BACKGROUND OF THE INVENTION

1. Field of the Invention

The ability to be able to detect a wide variety of compounds at extremely low concentration with great specificity has provided substantial advances in diagnostic monitoring of drug administration.

In many fields, immunoassays have found application in detecting trace amounts of individual substances. The immunoassays are characterized by being able to detect a single substance at very low concentrations. However, in many situations, it is desirable to further increase the sensitivity. Other considerations involve minimizing background or unmodulatable signal, simplifying synthesis of the reagents; allowing for automation and finding application on a wide variety of conventional instruments and providing a simple protocol.

Among the immunoassays which have found widespread use are homogeneous enzyme immunoassays and homogeneous fluorescent immunoassays, where homogeneous intends the avoidance of a separation step in the assay, rather than having a single phase. These assays have found widespread acceptance and commercialization. However, there are still opportunities for further improvements in these assays in accordance with the above criteria or providing alternatives which may find preferred application in specific situations.

2. Description of The Prior Art

U.S. Pat. Nos. 4,256,834, and 4,275,149 and references included therein are illustrative of immunoassays. U.S. Pat. Nos. 3,855,987 and 4,108,972 describe labeled particles, particularly fluorescent labeled particles.

SUMMARY OF THE INVENTION

A specific binding pair assay is provided involving a fluorescent bead to which is conjugated a member of a specific binding pair and, preferably, also a label, normally a catalyst, which is a component of a signal producing system, which system also includes the fluorescent bead. A second conjugate involves a catalyst, normally an enzyme, and a member of the specific binding pair, so that the amount of catalyst which binds to the fluorescent bead through the intermediacy of the specific binding of the specific binding pair members is related to the amount of analyte in the assay medium. Upon becoming bound to the particle, the catalyst, itself or in conjunction with the label conjugated to the particle, produces a product which results in quenching of the fluorescent bead in proportion to the amount of second conjugate catalyst bound to the bead. Unbound catalyst does not produce a product that causes quenching. Thus, the residual fluorescence will be related to the amount of analyte in the medium.

DESCRIPTION OF THE SPECIFIC EMBODIMENTS

A method is provided for determining low concentrations of organic compounds in a wide variety of media, particularly organic compounds having physiological activity. The compounds are naturally present in physiological fluids or administered to vertebrates. The subject method employs in an assay medium a continuous liquid phase and a discontinuous solid phase, comprised of discrete small particles having relatively slow settling rates and being capable of being stably dispersed in the medium during the period of the assay, preferably longer.

The assay reagents include particles which are small inert beads, which are highly fluorescent due to the presence of a plurality of fluorescent chromophoric groups. A member of a specific binding pair and preferably, also a component of a signal producing system, are conjugated to the fluorescent particle. Also included as an assay reagent is a catalyst, normally an enzyme, conjugated to a specific binding pair member, either directly or indirectly. When the catalyst binds to the fluorescent particle through the intermediacy of binding of specific binding pair members, the catalyst, by itself or in combination with the label conjugated to the particle, produces a product which binds to the particle resulting in the quenching of the fluorescent beads. The reduction in fluorescence of the particles can be related to the amount of analyte in the assay medium by employing standards having known amounts of analyte.

The analyte will be a member of a specific binding pair consisting of ligand and its homologous receptor. The solid phase particles or beads will be bound, directly or indirectly, covalently or non-covalently, to one of the members of the specific binding pair. There is an exception where a specific type of receptor to a specific ligand is the analyte. Three specific binding components are required, viz. receptor, antireceptor or ligand for the receptor, which may be bound to the particle, and ligand for the receptor or antireceptor respectively. Thus the receptor as an analyte allows for a number of alternative conjugates. In addition, a catalytic member of the signal producing system will be bound or become bound to the reciprocal member of the specific binding pair. By appropriate choice of specific binding pair conjugates, the amount of signal producing member bound to the particle can be related to the amount of analyte in the assay medium.

In carrying out the method, one combines the analyte containing sample, the fluorescent particle conjugate, the catalyst labeled specific binding pair member, as well as additional reagents, such as enzyme substrates, redox reactants, polyvalent specific binding pair members, etc., and determines the signal from the assay medium. By comparing the observed signal with the signal obtained from an assay medium having a known amount of analyte, one can qualitatively or quantitatively determine the amount of the analyte of interest.

In performing the subject method, there will be at least two reagents, namely, the fluorescent particle conjugate; and the catalyst-specific binding pair member conjugate. These conjugates will vary depending upon the nature of the analyte, the particular signal producing system employed, and the nature of the particle.

DEFINITIONS

Analyte—The compound or composition to be measured, which may be a ligand, which is mono- or polyepitopic, antigenic or haptenic, a single or plurality of compounds which share at least one common epitopic site or a receptor.

Specific Binding Pair Members ("mip")—Two different molecules where one of the molecules has an area on the surface or in a cavity which specifically binds to a particular spatial and polar organization of the other molecule. The members of the specific binding pair are ligand and receptor (antiligand). For the most part, the ligand and antiligand will be members of an immunological pair consisting of ligand and antibody and as a convenient shorthand notation, each member will be referred to as a mip.

Ligand—Any organic compound for which a receptor naturally exists or can be prepared.

Receptor ("antiligand")—Any compound or composition capable of recognizing a particular spatial and polar organization of a molecule i.e. epitopic site. Illustrative receptors include naturally occurring receptors, e.g. thyroxine binding globulin, antibodies, enzymes, Fab fragments, lectins and the like.

Ligand Analog—A modified ligand which can compete with the analogous ligand for a receptor, the modification providing means to join a ligand analog to another molecule. The ligand analog will normally differ from the ligand by more than replacement of a hydrogen with a bond which links the ligand analog to a hub or label.

Poly(ligand-analog)—a plurality of ligands or ligand analogs joined together covalently, normally to a hub nucleus. The hub nucleus is a polyfunctional material, normally polymeric, usually having a plurality of functional groups e.g. hydroxy, amino, mercapto, ethylenic, etc. as sites for linking. The hub nucleus may be water soluble or insoluble, preferably water soluble, and will normally be at least about 35,000 molecular weight and may be 10 million or more molecular weight, but usually under 600,000, more usually under 300,000. Illustrative hub nuclei include polysaccharides, polypeptides (including proteins), nucleic acids, ion exchange resins and the like. Water insoluble hub nuclei can be the same as those indicated for the particle.

Particle—The particle is a discrete solid particle, which may be swelled or remain unswelled by the liquid phase, and composed of a wide variety of both hydrophobic and hydrophilic materials. The particle will be solid, hollow or porous, normally solid or reticulated, having a substantially smooth or irregular surface, and having a plurality of fluorescent chromophores covalently or non-covalently, substantially permanently bound to the particle. The particles will be at least partially transparent to light in a portion of the wave length range between 300 and 800 nm.

Signal Producing System—The signal producing system will have at least three components: (1) a fluorescent particle; (2) a catalyst, normally an enzyme; and (3) a reactant which is transformed, directly or indirectly, to a product which is capable of binding to the fluorescent particle to reduce the fluorescent emission from the particle. The other members of the signal producing system will depend upon the nature of the catalyst e.g. enzymatic or non-enzymatic, whether a single catalyst or two or more catalysts are used, and the like. The result of the signal producing system is to preferentially produce a product in the environment of the fluorescent particle which quenches the fluorescence. The degree of quenching is in proportion to the amount of analyte in the assay medium.

Label—The label may be any molecule conjugated to another molecule and is arbitrarily chosen as to which molecule is the label. In the subject invention, the label will be the mip conjugated to the particle, and members of the signal producing system conjugated to either the particle or mips.

Particle Conjugate—The fluorescent particle to which is bound, directly or indirectly, a mip.

Catalyst-particle Label—The catalyst-particle label may be any catalyst which together with the catalyst of the catalyst-mip conjugate can produce a molecule providing quenching of fluorescence (quenching of the fluorescent bead), usually by deposition of a material optically dense at the excitation or fluorescent emission wave length of interest. The catalyst-particle label is the catalyst bound to the particle, either covalently or non-covalently. Where the catalyst is an enzyme it will be referred to as the "enzyme-particle label."

Catalyst-mip Conjugate—A conjugate between a catalyst which is a member of a specific binding pair and ligand or antiligand. The choice of ligand or antiligand will depend upon the analyte of interest and the particular protocol for the assay. One or more mips may be bound to a catalyst or one or more catalysts bound to a mip.

METHOD

The subject assay is carried out in an aqueous zone at a moderate pH, generally close to optimum assay sensitivity, without separation of the assay components or products. The assay zone for the determination of analyte is prepared by employing an appropriate aqueous medium, normally buffered, the unknown sample, which may have been subject to prior treatment, the particle conjugate, the enzyme-mip conjugate, all of the materials required for the signal producing system for producing a detectable signal, as well as members of the specific binding pair or their analogs, as required.

The presence of ligand or its homologous receptor ("antiligand") in the unknown will affect the partition of the signal producing system between the immediate environment of the particle or solid phase and the bulk solution in the assay medium.

In carrying out the assay, an aqueous medium will normally be employed. Other polar solvents may also be included, usually oxygenated organic solvents of from 1–6, more usually from 1–4 atoms, including alcohols, ethers and the like. Usually these cosolvents will be present in less than about 40 weight percent, more usually in less than about 20 weight percent.

The pH for the medium will usually be in the range of about 4–11, more usually in the range of about 5–10, and preferably in the range of about 6.5–9.5. The pH is chosen so as to maintain a significant level of specific binding by the receptor while optimizing signal producing efficiency. In some instances, a compromise will be made between these two considerations. Various buffers may be used to achieve the desired pH and maintain the pH during the determination. Illustrative buffers include borate, phosphate, carbonate, tris, barbital and the like. The particular buffer employed is not critical to this invention but in individual assays, one buffer may be preferred over another.

Moderate temperatures are normally employed for carrying out the assay and usually constant temperatures during the period of the measurement, particularly for rate determinations. The temperatures for the determination will generally range from about 10°–50° C., more usually from about 15°–40° C.

The concentration of analyte which may be assayed will generally vary from about $10^{-4}$ to $10^{-15}$ M, more usually from about $10^{-6}$ to $10^{-13}$ M. Considerations such as whether the assay is qualitative, semi-qualitative or quantitative, and the concentration of the analyte of interest will normally determine the concentration of the other reagents.

While the concentrations of the various reagents in the assay medium will generally be determined by the concentration range of interest of the analyte, the final concentration of each of the reagents will normally be determined empirically to optimize the sensitivity of the assay over the range of interest. The total binding sites of the members of the specific binding pair which are reciprocal to the analyte will not be less than about 0.1 times the minimum concentration of interest based on binding sites of analyte and usually not more than about 1,000 times the maximum concentration of interest based on analyte binding sites, usually about 0.1 to 100 times, more usually about 0.3–10 times the maximum concentration of interest. By concentration is intended the available concentration, that is, the concentration at saturation, and not necessarily the actual concentration where members of the specific binding pair may not be equally available for binding. The number of particles will vary based on the number of bound mips, the required sensitivity and the need to have the excitation light pass through the medium without significant reduction in intensity.

Depending upon the particular signal producing system as well as the manner in which the mips are employed, the amount of the various reagents may be varied widely. For example, there is the situation where the analyte has a plurality of binding sites, such as with an antigen and an antibody, and is used as a bridge to bind the complementary mips resulting in binding of the catalyst conjugate to the particle. In this situation, greater excesses of the catalyst conjugate could be used than in a competitive situation where the analyte is the same mip as the mip of the catalyst-mip conjugate.

For the most part, large excesses of reagents will not be desirable, although permissible. Usually one would not wish to have significant reaction occurring in the bulk medium as compared to the reaction at the particle surface. However, since the subject method requires diminution of the fluorescence by interaction of a substrate product with the fluorescent particle, a significant amount of substrate product can be tolerated in the bulk medium. The amount of substrate product capable of quenching produced in the bulk medium can be further reduced by adding one or more scavengers which interfere with the reaction catalyzed by the catalyst-mip conjugate. Where the analyte acts as a bridge, relatively high excesses of mip would be permissible on the particle, so as to ensure that substantially all of the analyte in the assay medium becomes bound to the particle.

The order of addition of the various reagents may be varied depending upon the particular protocol and analyte. Also affecting the order of addition is whether the equilibrium mode or rate mode is employed in the determination.

Since with many receptors, the association of the mips is almost irreversible during the time period of the assay, where the two conjugates are reciprocal mips, one will normally avoid combining the fluorescent particle conjugate with the catalyst-mip conjugate prior to the addition of the analyte. By contrast, where the two conjugates have the same mip, one could combine them prior to introduction of the unknown sample into the assay medium. Regardless of the nature of the analyte, all the reagents can be added simultaneously and either a rate or equilibrium determination made.

An additional variant is whether monoclonal or polyclonal antibodies are employed. Monoclonal antibodies bind to a single haptenic or epitopic site of an antigen, which has a plurality of epitopic sites. Therefore, the antigen may be treated as monoepitopic as to each monoclonal antibody. Thus, for example, if monoclonal antibodies are used, and monoclonal antibodies to an epitopic site are conjugated to the particle and monoclonal antibodies to a different epitopic site are conjugated to the catalyst, it would be feasible to incubate the antigenic analyte with the particle conjugate prior to addition of the catalyst-mip conjugate. This would not be true with polyclonal sera.

One or more incubation steps may be involved in preparing the assay medium. For example, it may be desirable to incubate an antigen analyte with the fluorescent particle conjugate. In addition, it may be desirable to have a second incubation after addition of the catalyst-mip conjugate before the addition of reactants, e.g. enzyme substrates. Whether to employ an incubation period and the length of the incubation period will depend to a substantial degree on the mode of determination -rate or equilibrium and the rate of binding of the mips. Usually, incubation steps will vary from about 0.5 min to 6 hrs, more usually from about 5 min to 1 hr. Incubation temperatures will generally range from about 4°–50° C., more usually from 15°–40° C.

After all the reagents of the signal producing system have been combined in combination with the analyte, the signal will then be determined. The method of determination will be by excitation of the fluorescent particles at a wave length absorbed by the fluorescent particles and by reading the fluorescent emission. The particles may be present in or separated from the assay medium by any convenient means and then read for fluorescent emission. Various conventional fluorimeters may be employed. Desirably, absorption of the fluorophore will be at a wave length greater than about 350 nm, preferably greater than about 400 nm, with emission at greater than about 400 nm, preferably greater than about 450 nm.

The temperature at which the signal is observed will generally range from about 10°–50° C., more usually from about 15°–40° C.

Standard assay media can be prepared which have known amounts of the analyte. The observed signals for the standard assay media may then be plotted, so as to relate concentration to signal. Once a standard curve has been established, a signal may be quantitatively related to the concentration of the analyte.

The time for measuring the signal will vary depending upon whether a rate or equilibrium mode is used, the sensitivity required, the particular fluorescer and the like. For a rate mode, the times between readings will generally vary from about 5 sec to 6 hrs, usually about 10 sec to 1 hr. For an equilibrium mode, after a steady state is achieved, a single reading may be sufficient or two readings over any convenient time interval may suffice.

The reactants will normally be added in substantial excess over the amount required during the course of the assay to avoid having the reactants rate limiting. Usually, the reactants will be at least in 1.5 fold excess over the maximum amount which would react at the extreme of analyte concentration. More usually there will be at least 2 fold excess, and the excess may be 5 fold or greater. During the course of the assay, the amount of the reactants provided must produce sufficient amount of quenching material to modulate the fluorescent signal.

MATERIALS

The components employed in the assay will be the fluorescent particle conjugate, the catalyst-mip conjugate, the remaining members of the signal producing system, which will normally be limited to reactants, such as substrates, cofactors and redox reactants, the analyte, and, as appropriate, combinations of mips, such as poly(ligand analog) and polyvalent receptor. Employed in the preparation of the reagents, will be particles, beads or microspheres, and the catalysts conjugated to the particle and mip.

Analyte

The ligand analytes of this invention are characterized by being monoepitopic or polyepitopic, haptenic or antigenic. The polyepitopic ligand analytes will normally be poly(amino acids) i.e. polypeptides and proteins, polysaccharides, nucleic acids, and combinations thereof. Such combinations or assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight. Among the hormones of interest, the molecular weights will usually range from about 2,000 to 60,000 molecular weight.

The wide variety of proteins may be considered as to the family of proteins having similar structural features, proteins having particular biological functions, proteins related to specific microorganisms, particularly disease causing microorganisms, etc.

The monoepitopic ligands will generally be from about 100 to 2,000, more usually 125 to 1000 daltons. The monoepitopic analytes will usually be naturally occurring or synthetic drugs, metabolites, pesticides, pollutants, and the like.

A number of ligands are set forth in U.S. Pat. No. 4,275,149, beginning at column 12, line 16 and terminating at column 18, line 44. This disclosure is incorporated herein by reference.

Ligand Analog

The ligand analog has been amply described in the aforementioned U.S. Pat. No. 4,275,149, the description beginning at line 47 and continuing to column 19, line 35, which disclosure is incorporated herein by reference.

Signal Producinq System

The signal producing system is predicated on the ability to modulate a fluorescent signal emanating from a particle by the binding to the particle of a plurality of molecules which are optically dense at the wavelength range of absorption or fluorescence emission of the particle. This is achieved by employing a catalyst bound to a mip and a reactant, usually of relatively low molecular weight, which is transformed, either directly or indirectly, to an insoluble product which is optically dense at a wavelength of interest. The signal producing system may be divided into various catagories, whether one or a plurality, usually two, catalysts are used, and whether the system involves enzymatic, non-enzymatic or a combination of such catalysts.

The first system which will be described employs a single catalyst. The catalyst may be enzymatic or non-enzymatic. For enzyme catalysts a substrate is employed which results in an insoluble optically dense molecule which binds to the particle. The substrate undergoes a transformation which changes both its solubility and light absorption characteristics.

The substrate will be a water soluble molecule, having relatively low light absorption above 500nm, non-fluorescent and generally of from about 150 to 1000 daltons. The change in properties may be as a result of hydrolysis to remove a water solubilising group resulting in an oxide anion which is part of a chromophore or a redox reaction resulting in a new chromophoric group having the desired properties, or other reaction.

To further accentuate the difference between optically dense product depositing onto the particle from the bulk solution or from optically dense product resulting from catalyst bound to the particle, combinations of catalysts can be used. One of the catalysts is bound to the particle and the other is bound to a mip. Usually, at least one of the catalysts will be an enzyme and preferably there will be an enzyme bound to a mip as the catalyst-mip conjugate. The catalyst-mip conjugate binds to the particle in proportion to the amount of analyte in the medium. The two catalysts interact in that the product of one is the reactant of the other. Since the two catalysts are held in close proximity at the particle surface when the catalyst-mip conjugate binds to the homologous mip at the particle surface, there is preferential production of the optically dense product at the particle surface. In effect, a concentration gradient is provided of the product of the catalyst bound to the particle, with the concentration diminishing with distance from the particle.

Where two enzymes are involved, preferably the enzyme bound to the particle—enzyme-particle label—will produce as its product the substrate for the enzyme of the enzyme-mip conjugate. By this way, one is insured of establishing an enhanced concentration of the substrate for the enzyme-mip conjugate at the particle surface. Where one enzyme is involved and a non-enzymatic catalyst, usually the enzyme will be conjugated to the mip.

Where a non-enzymatic catalyst is involved, it will ordinarily be a compound which can undergo either one or two election transfers. By employing two different reactants, which cannot react with each other, due to their electron transfer requirements, the catalyst acts as an intermediary in transferring elections from one reactant to the other reactant.

The differentiation between reaction in the bulk medium and at the particle surface can be further enhanced by providing for a scavenger in the bulk aqueous medium which reacts with the product of one catalyst, which product serves as a reactant for the other catalyst.

Besides the interaction involving two catalysts, there is also the interaction is between the fluorescent chromophore present in the particle and the quenching product of the enzyme reactions. While conveniently, the quenching product may be black, it will suffice that the quenching product be optically dense in the wavelength range of absorbance or fluorescence of the fluorophore present in the particle.

The quenching product may be either water insoluble or slightly water soluble, may preferentially absorb to the particle as compared to diffusing in the bulk aqueous medium, or may interact with a reactant in the aqueous medium, resulting in the deposition or binding of an optically dense product onto the particle.

A wide variety of compounds may serve as the optically dense product. For example, insoluble dyes having a phenoxide group which is part of the chromophore may be capped with esters, both organic and inorganic, e.g. acetate, butyrate and phosphate, or glycosidyl ethers e.g. β-galactosidy and β-glucosidyl. The capping fulfills two functions: enhances water solubility and changes the chromophoric properties of the dye, resulting in light absorption at shorter wavelengths. The capping group may then be removed by the enzyme of the enzyme-mip conjugate.

Compounds of interest include alizarin, Martius yellow, 4-phenyldiazonaphthol-1, etc.

Alternative compounds are those which undergo a redox reaction to become insoluble and optically dense. Illustrative compounds include iodonitrotriphenyltetrazolium salts (INT) to form formazan, 2,5-dichlorophenol-indophenol to insoluble dye, 4-chloronaphthol to dye, etc.

The following table illustrates a number of different enzymes which may be employed for producing a quenching molecule.

TABLE I

| First* Enzyme | Second Enzyme | Substrate | Signal Quencher |
|---|---|---|---|
| 1. Galactose oxidase | horse radish peroxidase | β-D-galactose | 4-Cl—1-naphthol dye |
| 2. uricase | horse radish peroxidase | urate | o-dianisidine dye |
| 3. glucose oxidase | microperoxidase | β-D-glucose | bis-toluidine dye |
| 4. alkaline phosphatase | peroxidase | 4-Cl—1-naphthyl phosphate | 4-Cl—1-naphthol dye |
| 5. hexokinase | glucose-6-phosphate dehydrogenase | glucose | iodonitrotriphenyl formazan |

*The first enzyme is arbitrarily indicated as being conjugated to the particle.

The enzymes which are used will fall for the most part into the classes oxidoreductases and hydrolases. Of particular interest is when two oxidoreductases are employed together. In a preferred embodiment, one of the enzymes produces hydrogen peroxide which is a substrate for the other enzyme. The other enzyme then catalyzes the reaction between hydrogen peroxide and an insoluble dye precursor, particularly a phenol or aryl amine.

Where a non-enzymatic catalyst is employed the systems will be somewhat more restricted. A preferred system is NADH or NADPH, meldola blue or phenazine methosulfate and INT, where the NADH or NADPH may be added or produced enzymatically from the oxidized counterparts.

A wide variety of fluorescers may be employed in conjuction with the particles. Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolylbenzene, 1,2-benzoxazole, bis-3-aminopyridinium salts, hellebrigenin, tetracycline, sterophenol, benzimidazolylphenylamine, 2-oxo-3-chromen, indole, xanthene, 7-hydroxycoumarin, phenoxazine, salicylate, strophanthidin, porphyrins, triarylmethanes and flavin.

Individual fluorescent compounds which have functionalities for linking or can be modified to incorporate such functionalities include dansyl chloride, fluoresceins such as 3,6-dihydroxy-9-phenylxanthhydrol, rhodamineisothiocyanate, N-phenyl 1-amino-8-sulfonatonaphthalene, N-phenyl 2-amino-6-sulfonatonaphthalene, 4-acetamido-4-isothiocyanatostilbene-2,2'-disulfonic acid, pyrene-3-sulfonic acid, 2-toluidinonaphthalene-6-sulfonate, N-phenyl, N-methyl 2-aminonaphthalene-6-sulfonate, ethidium bromide, atebrine, auromine-0, 2-(9'-anthroyl)palmitate, dansyl phosphatidylethanolamine, N,N'-dioctadecyl oxacarbocyanine, N,N'-dihexyl oxacarbocyanine, merocyanine, 4-(3'-pyrenyl) butyrate, d-3-aminodesoxyequilenin, 12-(9'-anthroyl)stearate, 2-methylanthracene, 9-vinylanthracene, 2,2'-(vinylene-p-phenylene)bis-benzoxazole, p-bis[2-(4'-methyl-5'-phenyloxazolyl)]benzene, 6-dimethylamino-1,2-benzophenazin, retinol, bis-(3'-aminopyridinium) 1,10-decandiyl diiodide, sulfonaphthyl hydrazone of hellebrigenin, chlortetracycline, N-(7-dimethylamino-4-methyl-2-oxo-chromenyl) maleimide, N-[p-(2-benzimidazolyl)phenyl]maleimide, N-(4-fluoranthyl) maleimide, bis(homovanillic acid), resazruin, 4-chloro-7-nitro-2.1.3-benzooxadiazole, merocyanine 540, resorufin, rose bengal, and 2,4-diphenyl-3(2H)-furanone.

It should be noted that the absorption and emission characteristics of the bound dye may differ from the unbound dye. Therefore, when referring to the various wavelength ranges and characteristics of the dyes, it is intended to indicate the dyes as employed and not the dye which is unconjugated and characterized in an arbitrary solvent.

The fluorescers may be bound to the particles internally or on the surface. The fluorophore groups may be introduced as a monomeric component in a copolymer through covalent bonding to functionalities internal to the particle or on the surface or by bonding to molecules which are in turn bonded to the particle, e.g. mips.

Particles

A wide variety of particles may be employed, which are swellable or non-swellable by the aqueous medium, which are porous, hollow or solid. The porous particles should have a sufficiently large pore size so as to allow for the ready diffusion of the various components of the signal producing system and the analyte through the particles. Therefore, for pore sizes the cut off size should be not less than about 200,000 daltons, preferably higher.

The size of the particle is limited by the following considerations. The particles should be capable of being relatively stably dispersed during the time of the assay and preferably longer. Indefinite stability in the assay medium is not required. The particle size should be sufficiently small, so that a larger number of particles will be in the solution. That is, one does not wish to see wide fluctuations in the signal caused by statistical fluctuations in the number of particles passing through the light path. Therefore, for the most part, the particles will be of a diameter in the range of about 50nm to 100μ, more usually about 500nm to 25μ. Pore sizes will generally vary from about 0.1 nm to under 750 nm, more usually not more than about 500 nm.

The particle size can be varied and the surface area increased by breaking larger particles into smaller particles by mechnical means, such as grinding, sonication, agitation, etc.

The particles can be derived from naturally occurring materials, naturally occurring materials which are synthetically modified and synthetic materials. Of particular interest are polysaccharides, particularly crosslinked polysaccharides, such as agarose, which is available as Sepharose, dextran, available as Sephadex and Sephacyl, cellulose, starch and the like. Other materials include polyacrylamides, polystyrene, polyvinyl alcohol, diatoms, copolymers of hydroxyethylmethacrylate and methyl methacrylate, silicones, glasses, available as Bioglas, and the like.

The particles should be polyfunctional or be capable of being polyfunctionalized. A wide variety of functional groups are available or can be incorporated. Functional groups include carboxylic acids, aldehydes, amino groups, cyano groups, ethylenic groups, hydroxyl groups, mercapto groups, and the like. The manner of linking a wide variety of compounds to the various particles is well known and is amply illustrated in the literature. See, for example, Cuatrecases, J. Biol. Chem. 245,3059 (1970).

The length of the linking groups will vary widely depending upon the nature of the compound being linked, the effect of the distance between the label and the particle on the properties of the label, the potential for crosslinking of the label, and the like. With each label, a preferred distance may be determined empirically.

Particle Conjugate

The fluorescent particle conjugate will always include a mip conjugated to the particle and optionally, a catalyst. When the catalyst is an enzyme, it is preferably the first enzyme. The conjugation may be direct or indirect. By direct conjugation is intended covalent bonding of the mip to the particle. Alternatively, one can employ receptor for the mip. Where the mip is multivalent an impure preparation of a complementary member may be covalently bonded to the particle. Noncovalent binding of the unpurified mip then gives a particle labeled with the mip free of contaminants. In some instances adsorption of the mip to the particle will suffice.

The catalyst will also be conjugated to the particle, either directly or indirectly. Various techniques have been developed for covalently conjugating enzyme catalysts to solid surfaces without significant deterioration of enzymatic activity. Depending upon the nature of the particle, various linking groups may be employed, the chains being generally less than about 20 atoms, more usually less than about 12 atoms. For nonenzymatic catalysts, there are ample procedures described in the literature.

In some situations, rather than involving a single complementary pair of mips, two complementary pairs of mips will be involved, where one mip is common to the two pairs. For example, where the analyte is a receptor such as IgE, one could covalently bond an allergen recognized by the IgE to the particle. The enzyme-mip could then employ as the mip, sheep anti(IgE) antibody. In the assay, the IgE analyte would bind to the allergen on the particle and the signal label conjugate [anti(IgE)] would bind to the IgE bound to the particle. This situation differs from the general situation since the binding of the analyte to the particle during the assay produces what has been defined as the particle conjugate. Also, other receptors such IgA, IgG, IgM, enzymes, specific receptors for ligands, such as estriol, biotin or other drugs, may be similarily employed.

The ratio of the number of mips to the molecular weight of the particle will vary widely, depending upon the nature of the particle, the available surface area, the protocol of the assay, and the like. The assay is predicated on preferentially producing an optically dense insoluble product at the particle surface. In a single catalyst system this results by having catalyst adjacent the surface produce an insoluble product which binds to the particle surface. The production of insoluble product is either inhibited in the bulk medium or such bulk medium formed insoluble product does not bind appreciably to the particle surface.

In the two catalyst system, the amount of insoluble product produced in the bulk medium is further reduced by providing for high localized concentrations of an essential reactant or intermediate at the particle surface. The enhanced concentration is a result of its production at the surface, so that diffusion into the medium results in a substantial dilution, and the partial transformation of such intermediate into optically dense product, which further reduces the amount of the intermediate which is available in the bulk solution.

Since it is desirable in the assay to have a high localized concentration of a catalyst at the assay surface, a high mip to particle ratio will usually be employed. For antigens, greater than about 10% of the surface will be covered with mips, more usually greater than 20% or more, while with haptens at least about one percent of the surface should be covered. Usually, there will be at least about one mip per 75,000 daltons, more usually at least about one mip per 25,000 daltons and the maximum number will normally be determined empirically. Where there are two catalysts, there will also have to be a minimum number of catalysts bound to the surface, there usually being at least one catalyst per 10 mips, more usually at least about one catalyst per 5 mips, where the maximum number may also be determined empirically. Depending upon the sensitivity required, the degree of optimization can vary widely.

Enzyme-Mip Conjugate

The catalyst-mip conjugate will involve a catalyst, usually an enzyme, usually the second enzyme, conjugated to a mip, which may be either a ligand or a receptor. Conjugation of catalysts, including enzymes, to haptens and antigens has been amply developed in the literature and does not require exemplification here. See, for example, U.S. Pat. Nos. 3,817,837 and 4,275,149.

Depending upon the size of the ligand and the size of the catalyst, as well as the effect on sensitivity and catalyst activity, the ratio of ligand molecules to catalyst molecules will vary widely.

Ancillary Materials

For the most part, particular ancillary materials will include poly(ligand analogs) and polyreceptor, where a polyvalent (based on binding sites) reagent is desired to act as a bridge and the ligand or receptor is monovalent. Alternatively, it may be desired that by having a single ligand or receptor bind to the particle, a plurality of catalyst-mip conjugates may then bind to the particle. One would then employ labeled anti(immunoglobulin)- from a source xenogenic to the source of the analyte receptor.

Various hub nuclei can be used, both nuclei which have been described for the particles, as well as other nuclei, such as polypeptides, proteins, nucleic acids, synthetic polymers, and the like.

Also included will be the various substrates which are required including the precursor to the optically dense product. These will usually be employed in amounts which are non-rate limiting.

As a matter of convenience, the reagents can be provided as kits, where the reagents are in predetermined ratios, so as to substantially optimize the sensitivity of the assay in the range of interest. Conveniently, the reagents can be lyophilized, so that the reagents have long storage lives. In reconstitution of the reagents, the particle conjugate will normally be dispersed in an aqueous medium, desirably of substantially the same density as the particle, so that the particles remain substantially uniformly dispersed or dispersable. By employing high density additives or adjusting the density of the particles, the desired density relationship can be achieved.

The various reagents may be combined in the same or separate vials depending upon the particular protocol. The reagents will include the fluorescent particle conjugate, the catalyst-mip conjugate, the substrates, any ancillary reagents, such as poly(ligand analog) or polyreceptor, as well as buffer and stabilizers, such as microbicides, and proteins.

The materials will normally be lyophilized, and in some situations, it may be desirable to include all of the components in a single reagent in combination with an excipient e.g. mannitol.

The following examples are offered by way of illustration and not by way of limitation.

EXPERIMENTAL

All percents and parts not otherwise indicated are by weight, except for mixtures of liquids, which are by volume. All temperatures not otherwise indicated are in centigrade. The following abbreviations are employed: GO-glucose oxidase; EDAC-ethyl dimethylaminopropyl carbodiimide; HRP-horse radish peroxidase; PBS-phosphate buffered saline; FITC-fluorescein isothiocyanate; DMF-dimethyl formamide; NHS-N-hydroxy succinimide; o.n.-overnight.

EXAMPLE 1

Preparation of Fluorescent Polyacrylamide Beads With Antitheophylline Antibodies and Glucose Oxidase Into a reaction flask was introduced 70 mg Immunobeads (Bio-Rad, No. 170–5910; 1 ml swollen gel), 6 ml of 25 mM sodium phosphate, pH 6.3, 70 μl sheep antitheophylline antibodies (3.4 mg), 10 μl succinylated sheep IgG (50 μg, $^{14}$C, 19,272 cpm) and 123 μl of glucose oxidase amine (2.0 mg). The suspension was incubated for one hour at 4°, followed by the addition of 16 mg EDAC (Sigma E7750). The mixture was retained o.n. at 4° and the following day was spun, the residue collected, and the gel washed 5x with PBS, pH 7.0. The amount of GO bound was determined spectrophotometrically from the unbound amount, which indicated that 68% of the GO was bound to give 1.33mg GO bound per 1 ml packed beads. The binding of the succinylated sheep IgG was determined by determining the amount of unbound IgG based on the amount of $^{14}$C in the supernatant. There was found to be 1.95 mg of antibody per 1 ml packed beads. To 0.5 ml of packed beads in 4 ml of 0.1 M sodium carbonate, pH 9.0, was added 50 μl of FITC (1 mg/100 ml DMF) and the mixture allowed to stand at room temperature for 3 hrs. After centrifuging, the gel was washed 6X PBS, pH 7.0, to yield the desired fluorescent conjugated particle.

EXAMPLE 2

Conjugation of Theophylline and HRP

Into a reaction flask was introduced 8.1 mg of 1-methyl-3-(3'-carboxypropyl)xanthine, 3.8 mg of NHS, 6.7 mg EDAC and 125 μl DMF and the mixture allowed to stand o.n. at room temperature.

To four 1.3 ml samples of HRP-oxyamine (1 mg) in 0.1 M sodium carbonate, pH 9.0 was added varying amounts of the ester prepared above to provide for preparations having mole ratios of theophylline to HRP of 400; 200, and two of 100 each. Into the first reaction mixture (400 mole ratio) was added 0.217 ml of DMF and 66 μl of the above ester in 8.25 μl increments over a period of about 2 hrs. Into the second reaction mixture (200 mole ratio), 0.238 ml of DMF was added and 33 μl of the ester added incrementally in 8.25 μl increments. Into the third reaction mixture (100 mole ratio), 0.24 ml of DMF was added and 16.5 μl of the ester added in 8.2 μl increments, while in the final reaction mixtures (100 mole ratio), no DMF was added, and 8.25 μl of the ester was added in 2.1 μl increments. During the addition, the temperature was maintained at 0°, and the mixture then allowed to stand overnight at 4°.

The reaction mixtures were then worked up by chromatography on G-25 Sephadex with standard buffer. Folin and UV spectroscopic analysis indicated theophylline/HRP ratios of 6.9, 4.0, 1.6 and 2.1 respectively.

EXAMPLE 3

Preparation of Glucose Oxidase Amine

Glucose oxidase (Sigma, E.C. 1.1.3.4) was concentrated from 360 ml to 60 ml with Amicon PM10 membrane at a pressure below 30 psi. The concentrate of glucose oxidase was dialyzed twice against 4 L of water at 4°, filtered and shown spectrophotometrically to have a concentration of 32 mg/ml. To 51.5 ml of the glucose oxidase solution was added dropwise 5.15 ml of 0.2M sodium periodate, the reaction occurring over 25 min. The product was chromatographed on a 2.5×60 cm column of Sephadex G-50 using 2 mM sodium acetate pH 4.5, and the major glucose oxidase peaks pooled to yield 91.5 ml of a solution containing the aldehyde derivative. To the solution was added dropwise 6 ml of 3 M ethylene diamine in 0.2 M sodium carbonate, pH 9.5, and the reaction allowed to proceed for 3 hr. To the mix was then added about 3.9 ml of 10 mg/ml sodium borohydride, the mixture incubated overnight and then chromatographed to remove the sodium borohydride.

EXAMPLE 4

Preparation of HRP-Oxyamine

To 5 ml of 10 mg/ml HRP in 5 mM sodium acetate, pH 4.5 buffer, was added 50 ml 0.2 M sodium iodate and the mixture stirred for 30 min, followed by chromatography on a G-50 Sephadex column, eluting with 2 mM sodium acetate buffer, pH 4.5. The protein fractions were pooled to 29 ml, the mixture cooled to 4° and 2.9 ml of 0.2 M 2,2'-oxy-bis-ethylamine in 0.5 M carbonate buffer, pH 9.5 at 4° added. The pH of the mixture was adjusted to 9.5 with 1 N sodium hydroxide, stirred for 2 hrs and 3.52 ml of a 4 mg/ml sodium borohydride-water solution added and the mixture allowed to react for 3.5 hr, followed by chromatography through a Sephadex G-50 column.

The above procedure was repeated using 400 mg of HRP and 3.5 g of 2,2'-oxy-bis-ethylamine. No significant change in enzyme activity was observed between the native amine and the modified amine, which had about four additional amino groups.

EXAMPLE 5

Preparation of Succinylated Sheep IgG

Sheep IgG (2.0 ml, American Bio Components, 10.6 mg/ml) was dialyzed against 50 mM sodium phosphate, pH 8.0 o.n. To the retentate was added 24 ml of 14C-succinic anhydride in acetone (0.07 M, 0.05 mCi NEN, NEC-621, Lot 980–130) with stirring to provide a ratio of 5 μmole to 5mg protein. After allowing the reaction to proceed for 0.5 h at room temperature, 0.95 ml of 0.75 M hydroxylamine-HCl, pH 8.0, was added and the mixture allowed to react for 30 min at room temperature. The reaction mixture was then dialyzed 4×50 mM sodium phosphate, pH 8.0. Based on radioactive counting, approximately 5.2 succinyl groups were introduced per protein molecule.

To demonstrate the utility of the subject assay in assaying for theophylline, the following assay was carried out. An assay medium was prepared by combining 20 μl of the theophylline-HRP conjugate (400×) to provide a final concentration of 0.2 mg/ml, and 500 μl of buffer (0.1 M sodium phosphate, 0.2 M NaCl, 1 mg/ml bovine serum albumin, pH 7.3). To the mixture was then added either 10 μl of buffer or 10 μl of theophylline solution to provide a final concentration of 2 μg/ml, followed by 25 μl of a bead dispersion (2.5 μl packed) and 500 μl of buffer and the mixture allowed to stand for 20 minutes at room temperature. To the mixture was then added an additional 500 μl of buffer, which was 50 mM in glucose, and 4-chloro-1-naphthol in an amount to provide a final concentration of 200 μg/ml and the fluorescence observed at 10 minutes and 30 minutes. The following table indicates the results.

TABLE II

|  | Fluorescence | |
| --- | --- | --- |
|  | 10 min. | 30 min. |
| Control (beads only) | 953* |  |
| No theophylline | 536** | 527** |
| 2 μg/ml theophylline | 626** | 603** |

*average of four results
**average of three results

It is evident from the above results, that a sensitive assay is achieved which can be readily applied for the determination of a wide variety of ligands. The assay does not require a separation step and is highly sensitive in providing for a single event resulting in a substantial change in signal. Furthermore, by use of particles, one can employ heterogeneous mixtures of mips to bind to the particles and be assured that the particles are labeled with the desired mip without significant interference from the other materials.

Although the foregoing invention has been described in some detail by way of illustration and example for purposes of clarity of understanding, it will be obvious that certain changes and modifications may be practiced within the scope of the appended claims.

What is claimed is:

1. An assay method for determining the presence in a sample of an analyte which is a member of a specific binding pair ("mip") consisting of ligand and its homologous receptor;
   said method employing:
   (a) a continuous aqueous medium;
   (b) discrete dispersible fluorescent solid particles to which are conjugated a mip and a catalyst (A);
   (c) a signal producing system comprised of said fluorescent particle, said catalyst (A), a catalyst (B) conjugated to a mip to provide a catalyst-mip conjugate, and at least one reactant capable of being transformed by one of said catalysts, wherein when said catalyst-mip conjugate is bound to said fluorescent particle through the intermediacy of mip binding, a product is produced directly or indirectly as a result of the transformation of said reactant by one of said catalysts which product binds to said particle and diminishes the fluorescence from said particle;
   wherein the amount of said catalyst-mip conjugate which binds to said particle is related to the amount of analyte in said aqueous medium and one of said catalysts is an enzyme;
   said method comprising:
   combining in an aqueous assay medium,
   (a) said sample;
   (b) said particle, substantially uniformly dispersed in said medium;
   (c) said catalyst-mip conjugate;
   (d) the homologous mip, where the analyte, particle conjugate, and catalyst-mip conjugate have the same mip; and
   (e) at least one of said reactant and any remaining members of said signal producing system; and
   determining the level of fluorescence from said particles.

2. A method according to claim 1, wherein said particles are of a size in the range of about 50 nm to 100μ.

3. A method according to any of claims 1 or 2, wherein both of said catalysts are enzymes.

4. An assay method for determining the presence in a sample of an analyte which is a member of a specific binding pair ("mip") consisting of ligand and its homologous receptor;
   said method employing:
   (a) a continuous aqueous medium;
   (b) discrete dispersible fluorescent solid particles to which are conjugated a mip and enzyme (A);
   (c) a signal producing system comprised of said fluorescent particle, said enzyme (A), enzyme (B) conjugated to a mip to provide an enzyme-mip conjugate, and at least one enzyme substrate, wherein when said enzyme-mip conjugate is bound to said fluorescent particle through the intermediacy of mip binding, an enzymatic product is produced which binds to said particle and diminishes the fluorescence from said particle;
   wherein the amount of said enzyme-mip conjugate which binds to said particle is related to the amount of analyte in said aqueous medium;
   said method comprising:
   combining in an aqueous assay medium,
   (a) said sample;

(b) said particle, substantially uniformly dispersed in said medium;

(c) said enzyme-mip conjugate;

(d) the homologous mip, where the analyte, particle conjugate, and enzyme-mip conjugate have the same mip; and (e) at least one enzyme substrate and any remaining members of said signal producing system; and determining the level of fluorescence of said particle.

5. A method according to claim 4, wherein said particles are of a size in the range of about 50 nm to 100μ.

6. A method according to any of claims 4 or 5, wherein the fluorescer of said fluorescent solid particles absorbs at a wavelength greater than about 350nm.

7. A method according to any of claims 4 or 5, wherein at least one of said enzymes is an oxidoreductase.

8. A method according to claim 7, wherein said oxidoreductase is a peroxidase.

9. A method according to any of claims 4 or 5, wherein said mip conjugated to said fluorescent solid particles is an antibody.

10. A method according to any of claims 4 or 5 wherein said analyte is a hapten.

11. A method according to any of claims 4 or 5, wherein said analyte is an antigen.

12. An assay method for determining the presence in a sample of an analyte which is a member of a specific binding pair ("mip") consisting of ligand and its homologous receptor;

said method employing:

(a) a continuous aqueous medium;

(b) discrete dispersible fluorescent solid particles to which are conjugated a mip and an oxidase capable of producing hydrogen peroxide;

(c) a signal producing system comprised of said fluorescent particle, said oxidase, a peroxidase conjugated to a mip to provide a peroxidase-mip conjugate, substrate for said oxidase and an insoluble aryl dye precursor, wherein when said peroxidase-mip conjugate is bound to said fluorescent particle through the intermediacy of mip binding, an insoluble dye is produced which binds to said particle and diminishes the fluorescence from said particle; wherein the amount of said peroxidase-mip conjugate which binds to said particle is related to the amount of analyte in said aqueous medium; said method comprising: combining in an aqueous assay medium, (a) said sample; (b) said particle, substantially uniformly dispersed in said medium; (c) said peroxidase-mip conjugate; (d) the homologous mip, where the analyte, particle conjugate and peroxidase-mip conjugate have the same mip; and (e) said oxidase substrate, said aryl dye precursor, and any remaining members of said signal producing system; and determining the level of fluorescence of said particle.

13. A method according to claim 12, wherein said oxidase is glucose oxidase, said peroxidase is horse radish peroxidase, and said aryl dye precursor is 4-chloro-1-naphthol.

14. A method according to any of claims 12 or 13, wherein said mip bound to said particle is an antibody.

15. A method according to claim 13, wherein said analyte is a hapten.

16. A method according to claim 13, wherein said analyte is an antigen.

* * * * *